(12) United States Patent
McClure et al.

(10) Patent No.: US 8,165,696 B2
(45) Date of Patent: Apr. 24, 2012

(54) MULTIPLE-PRONGED IMPLANTABLE STIMULATOR AND METHODS OF MAKING AND USING SUCH A STIMULATOR

(75) Inventors: Kelly H. McClure, Simi Valley, CA (US); Matthew I. Haller, Valley Village, CA (US); Jay Daulton, Gilroy, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 939 days.

(21) Appl. No.: 11/066,968

(22) Filed: Feb. 25, 2005

(65) Prior Publication Data

US 2006/0195143 A1     Aug. 31, 2006

(51) Int. Cl.
*A61N 1/04* (2006.01)

(52) U.S. Cl. ........................... 607/116; 607/118

(58) Field of Classification Search .............. 607/118, 607/116
See application file for complete search history.

(56) References Cited

U.S. PATENT DOCUMENTS

| | | | |
|---|---|---|---|
| 3,866,615 A * | 2/1975 | Hewson | 607/4 |
| 5,144,960 A * | 9/1992 | Mehra et al. | 607/125 |
| 5,193,539 A | 3/1993 | Schulman et al. | |
| 5,193,540 A | 3/1993 | Schulman et al. | |
| 5,312,439 A | 5/1994 | Loeb | |
| 5,344,438 A * | 9/1994 | Testerman et al. | 607/118 |
| 5,405,367 A | 4/1995 | Schulman et al. | |
| 5,578,069 A * | 11/1996 | Miner, II | 607/126 |
| 6,051,017 A | 4/2000 | Loeb et al. | |
| 6,054,017 A | 4/2000 | Yang et al. | |
| 6,061,596 A | 5/2000 | Richmond et al. | |
| 6,164,284 A | 12/2000 | Schulman et al. | |
| 6,175,764 B1 | 1/2001 | Loeb et al. | |
| 6,181,965 B1 | 1/2001 | Loeb et al. | |
| 6,185,452 B1 | 2/2001 | Schulman et al. | |
| 6,185,455 B1 | 2/2001 | Loeb et al. | |
| 6,208,894 B1 | 3/2001 | Schulman et al. | |
| 6,214,032 B1 * | 4/2001 | Loeb et al. | 607/1 |
| 6,315,721 B2 | 11/2001 | Schulman et al. | |
| 7,450,998 B2 * | 11/2008 | Zilberman et al. | 607/118 |
| 2003/0036773 A1 * | 2/2003 | Whitehurst et al. | 607/3 |
| 2003/0204232 A1 * | 10/2003 | Sommer et al. | 607/122 |
| 2004/0186528 A1 * | 9/2004 | Ries et al. | 607/36 |
| 2009/0024196 A1 * | 1/2009 | Kuzma et al. | 607/116 |

* cited by examiner

*Primary Examiner* — Eric D. Bertram
(74) *Attorney, Agent, or Firm* — Frommer Lawrence & Haug LLP; Bruce E. Black

(57) ABSTRACT

An implantable stimulator includes a base, two prongs extending from the base and an electrode disposed on each of the prongs. This stimulator may be part of a system that includes an external device for transcutaneously communicating with the implanted stimulator. A method of using the implantable stimulator includes generating a current gradient between the electrodes on the two prongs to stimulate a target site in a patient. A method of making the implantable stimulator includes coating electrode material on the prongs except where the electrode surfaces are to be formed.

18 Claims, 6 Drawing Sheets

MULTIPLE-PRONGED IMPLANTABLE STIMULATOR AND METHODS OF MAKING AND USING SUCH A STIMULATOR

BACKGROUND

Implantable stimulators and microstimulators, also known as BION® devices (where BION® is a registered trademark of Advanced Bionics Corporation, of Valencia, Calif.), are typically characterized by a small, cylindrical housing which contains electronic circuitry that produces electric currents between spaced electrodes. These microstimulators are implanted proximate to target tissue, and the currents produced by the electrodes stimulate the tissue to reduce symptoms or otherwise provide therapy for various disorders. An implantable battery-powered medical device may be used to provide therapy for various purposes including nerve or muscle stimulation. For example, urinary urge incontinence may be treated by stimulating the nerve fibers proximal to the pudendal nerves of the pelvic floor; erectile or other sexual dysfunctions may be treated by providing stimulation of the cavernous nerve(s); and other disorders, e.g., neurological disorders caused by injury or stroke, may be treated by providing stimulation of other appropriate nerve(s).

By way of example, in U.S. Pat. No. 5,312,439, entitled Implantable Device Having an Electrolytic Storage Electrode, an implantable device for tissue stimulation is described. U.S. Pat. No. 5,312,439 is incorporated herein by reference in its entirety. The described microstimulator shown in the '439 patent relates to an implantable device using one or more exposed, electrolytic electrodes to store electrical energy received by the implanted device, for the purpose of providing electrical energy to at least a portion of the internal electrical circuitry of the implantable device. It uses an electrolytic capacitor electrode to store electrical energy in the electrode when exposed to body fluids.

Another microstimulator known in the art is described in U.S. Pat. No. 5,193,539, "Implantable Microstimulator", which patent is also incorporated herein by reference in its entirety. The '539 patent describes a microstimulator in which power and information for operating the microstimulator are received through a modulated, alternating magnetic field in which a coil is adapted to function as the secondary winding of a transformer. The induction coil receives energy from outside the body and a capacitor is used to store electrical energy which is released to the microstimulator's exposed electrodes under the control of electronic control circuitry.

In U.S. Pat. Nos. 5,193,540 and 5,405,367, which patents are incorporated herein by reference in their respective entireties, a structure and method of manufacture of an implantable microstimulator is disclosed. The microstimulator has a structure which is manufactured to be substantially encapsulated within a hermetically-sealed housing inert to body fluids, and of a size and shape capable of implantation in a living body with appropriate surgical tools. Within the microstimulator, an induction coil receives energy from outside the body requiring an external power supply.

In yet another example, U.S. Pat. No. 6,185,452, which patent is likewise incorporated herein by reference in its entirety, there is disclosed a device configured for implantation beneath a patient's skin for the purpose of nerve or muscle stimulation and/or parameter monitoring and/or data communication. Such a device contains a power source for powering the internal electronic circuitry. Such power supply is a battery that may be externally charged each day. Similar battery specifications are found in U.S. Pat. No. 6,315,721, which patent is additionally incorporated herein by reference in its entirety.

Other microstimulator systems prevent and/or treat various disorders associated with prolonged inactivity, confinement or immobilization of one or more muscles. Such microstimulators are taught, e.g., in U.S. Pat. No. 6,061,596 (Method for Conditioning Pelvis Musculature Using an Implanted Microstimulator); U.S. Pat. No. 6,051,017 (Implantable Microstimulator and Systems Employing the Same); U.S. Pat. No. 6,175,764 (Implantable Microstimulator System for Producing Repeatable Patterns of Electrical Stimulation; U.S. Pat. No. 6,181,965 (Implantable Microstimulator System for Prevention of Disorders); U.S. Pat. No. 6,185,455 (Methods of Reducing the Incidence of Medical Complications Using Implantable Microstimulators); and U.S. Pat. No. 6,214,032 (System for Implanting a Microstimulator). The applications described in these additional patents, including the power charging techniques, may also be used with the present invention. The '596, '017, '764, '965, '455, and '032 patents are incorporated herein by reference in their respective entireties.

SUMMARY

An implantable stimulator includes a base, two prongs extending from the base and an electrode disposed on each of the prongs. This stimulator may be part of a system that includes an external device for transcutaneously communicating with the implanted stimulator. A method of using the implantable stimulator includes generating a current gradient between the electrodes on the two prongs to stimulate a target site in a patient. A method of making the implantable stimulator includes coating electrode material on the prongs except where the electrode surfaces are to be formed.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

The present specification describes, among other things, a variety of new configurations for an implantable stimulator. The new configurations described herein allow the stimulator to be more easily implanted and secured in certain circumstances than previous stimulators. The new configurations also allow for the generation of different stimulation fields than were available previously.

As used herein and in the appended claims, unless otherwise specifically denoted, the terms "stimulator" and "microstimulator" will be used interchangeably to refer to any implantable medical device that may be implanted within a patient to provide a stimulus. As described above, an implanted stimulator may deliver an electrical current to surrounding tissue to stimulate that tissue for therapeutic purposes. Stimulators are also typically configured to transcutaneously communicate with an external device.

The stimulating current that is output by an implanted stimulator is not constant, but is delivered in a regular cycle. Consequently, there are a number of parameters that characterize the current that is output by the implanted stimulator. For example, the stimulating current will have a frequency, amplitude and pulse width. These parameters can be adjusted to tailor the stimulation to the needs of a particular recipient patient. The stimulating current may also be delivered in bursts and have a duty cycle that describes the length and frequency of the current bursts.

There are a wide variety of conditions that can be treated with a stimulator. For example, some patients receive a stimulator to control or mask chronic pain. In such patients, the stimulator may create a tingling sensation throughout a particular painful region of the body known as paresthesia. The size, intensity and character of the paresthesia may be controlled by adjusting the parameters of the stimulating current.

The following listed patents describe various details associated with the manufacture, operation, and use of BION implantable microstimulators, and are all incorporated herein by reference:

| Application/Patent/ Publication No. | Filing/ Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 6,185,452 | Issued Feb. 6, 2001 | Battery-Powered Patient Implantable Device |
| U.S. Pat. No. 6,164,284 | Issued Dec. 26, 2000 | System of Implantable Devices For Monitoring and/or Affecting Body Parameters |
| U.S. Pat. No. 6,208,894 | Issued Mar. 27, 2001 | System of Implantable Devices For Monitoring and/or Affecting Body Parameters |
| U.S. Pat. No. 6,054,017 | Issued Apr. 18, 2000 | Improved Implantable Microstimulator and Systems Employing Same |

Figure 1:
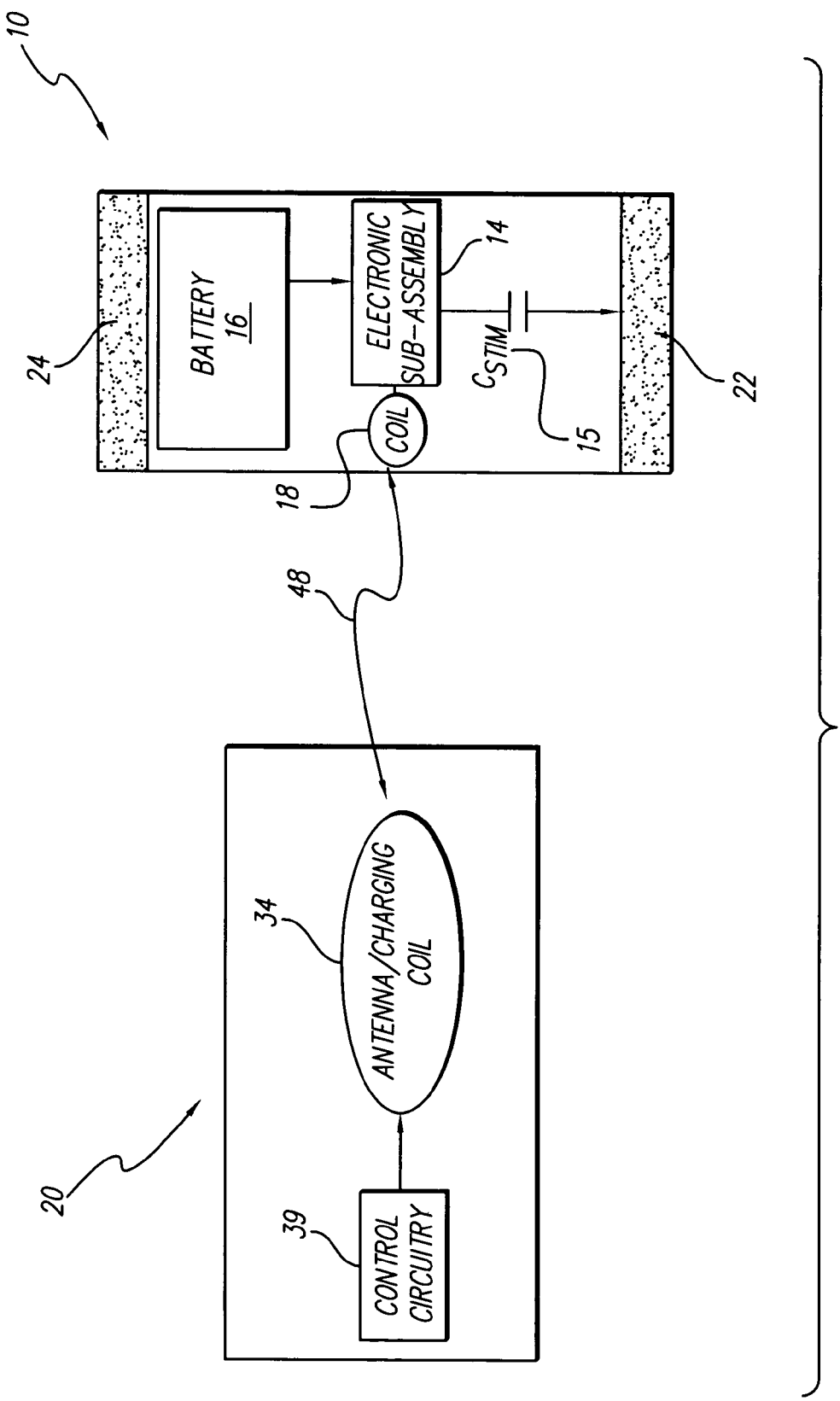
FIG. 1 is a diagram of a stimulator and external controlling device according to principles described herein.

FIG. 1 shows an exemplary implantable stimulator (10) and an exemplary external device (20). As will be described in more detail below, the external device (20) may take any of several forms, including, but not limited to, a base station and chair pad or a remote control unit.

The implantable stimulator (10) may be any type of implantable medical device. For example, the implantable stimulator (10) may be an implantable microstimulator. Microstimulators are smaller than conventionally sized stimulators and are more easily implanted in a patient. Microstimulators may be injected through a large bore needle or placed via a small incision in the skin. An exemplary, but not exclusive, implantable microstimulator is the BION® microstimulator (Advanced Bionics® Corporation, Valencia, Calif.) which may be configured to stimulate tissue to alleviate urinary incontinence, reduce pain, or otherwise provide therapy for various disorders. Other examples of implantable stimulators include, but are not limited to, spinal cord stimulators (SCS), cochlear implants, and deep brain stimulators.

The implantable stimulator (10) is implanted in the target tissue area of a patient and the external device (20) may be used to communicate with the stimulator (10). Such communication may include, but is not limited to, transcutaneously transmitting data to the stimulator (10), receiving data from the stimulator (10), providing power to a stimulator that does not contain a battery, transferring power to the rechargeable battery (16) in the stimulator (10), and/or providing recovery power to the rechargeable battery (16) when the battery has been depleted to zero volts.

As illustrated in FIG. 1, the stimulator (10) may include a number of components including a rechargeable battery (16) configured to supply the stimulator (10) with power. The battery (16) may be a primary battery, a rechargeable battery, a capacitor, or any other suitable power source. In some examples, however, no battery (16) is included, with the stimulator (10). In such a case, the stimulator is powered by the external device (20). In other examples, a stimulator may receive power from both an internal battery (16) and an external device (20).

The stimulator (10) also includes a coil (18) configured to receive and/or emit a magnetic field that is used to communicate with, or receive power from, the external device (20). Finally, the stimulator (10) includes a stimulating capacitor (15) and two or more electrodes (22, 24) configured to stimulate tissue with current. The stimulator (10) may include additional and/or different electronic components (14) configured to perform a variety of functions as best serves a particular application. One or more of these components may be housed within a case or housing, as shown, for example, in U.S. Pat. No. 5,193,539, issued Mar. 16, 1993, for an "Implantable Microstimulator," which patent is incorporated herein by reference in its entirety.

The exemplary external device (20) of FIG. 1 includes control circuitry (39) and an antenna/charging coil (34) configured to emit and/or receive a magnetic field that is used to communicate with the implantable stimulator (10). In one embodiment, the antenna/charging coil (34) and the stimulator's coil (18) communicate via a bidirectional telemetry link (48). The bidirectional telemetry link (48) may be known as a Radio Frequency (RF) telemetry link.

The external device (20) may be configured to perform any number of functions. For example, the external device (20) may be configured to transcutaneously charge the rechargeable battery (16) in the implanted stimulator (10). The external device (20) may also be configured to transcutaneously transmit data to the stimulator (10), receive data from the stimulator (10), and/or provide recovery power to the rechargeable battery (16) when the battery has been depleted to zero volts. The transmitted data may include configuration bits, programming bits, calibration bits, and/or other types of data. The signals that are sent between the external device (20) and the stimulator (10) may be modulated using frequency shift keying (FSK), on-off keying (OOK), or any other type of modulation scheme.

The functions performed by the external device (20) will vary as best serves the particular application of the stimulator (10) or the party using the external device (20). The shape and design of the external device (20) will likewise vary.

Conventionally, the stimulator (10) has been formed with a cylindrical housing, the electrodes (22 and 24) being located at opposite ends of the cylinder. This configuration has many advantages. For example, the configuration is easy to implant in the patient using, for example, a bore needle.

However, it has been discovered that a stimulator configuration that is shorter and wider, i.e., has a smaller aspect ratio, will also have advantages in certain instances. For example, with a cylindrical stimulator, the two electrodes (22 and 24), also referred to as the anode and cathode, are relatively far apart. This spacing limits the magnitude of the current gradient that can be created between the electrodes. In some circumstances, a large current gradient may be advantageous or necessary to provide the stimulation desired.

Consequently, several novel and advantageous stimulator configurations, and methods of making and using those stimulators, will be disclosed and described with respect to FIGS. 2-6. These new stimulator configurations will provide features that have not been available with conventional stimulators and that may be advantageous in particular patients as determined by a treating physician.

Figure 2:
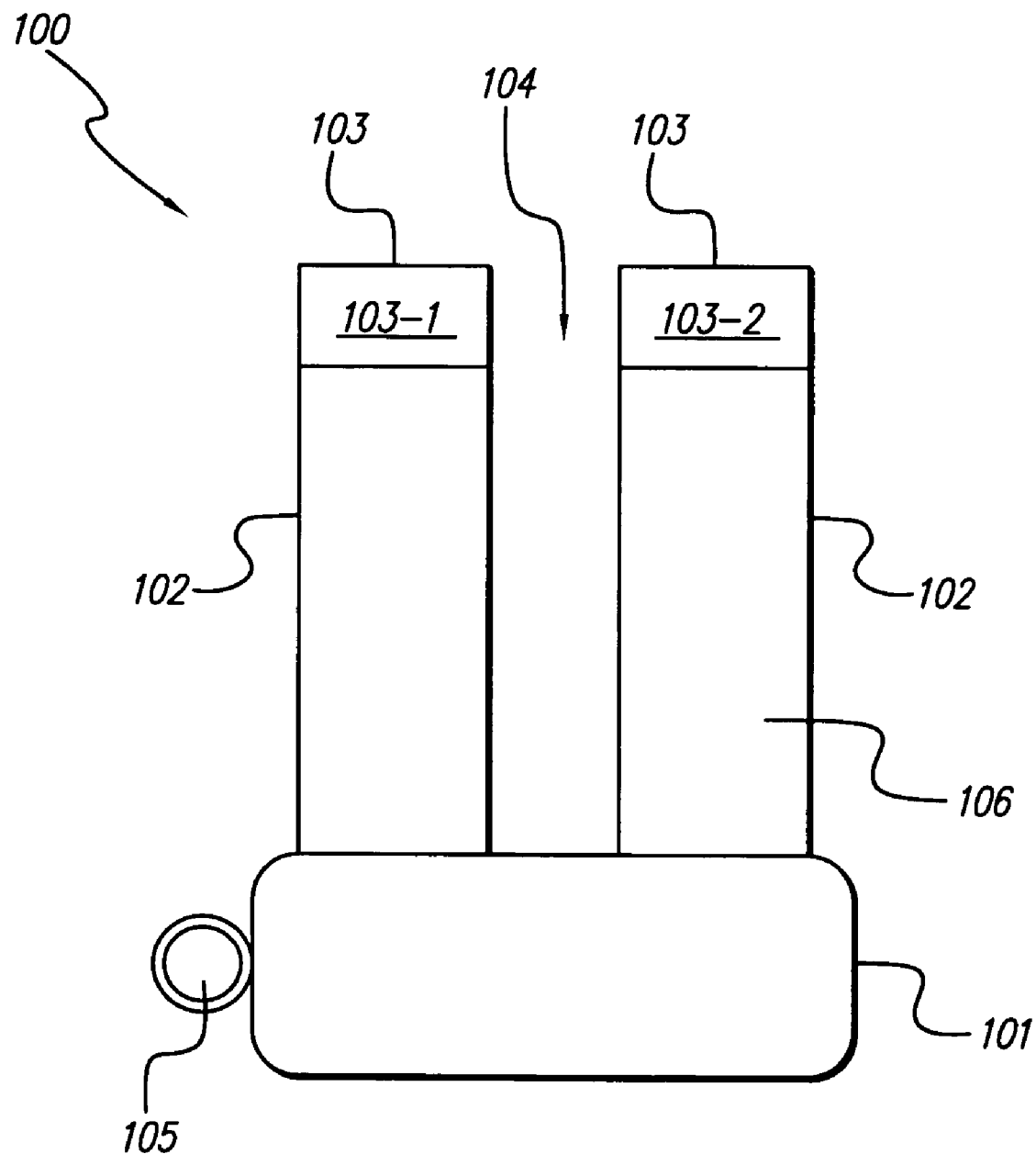
FIG. 2 illustrates a stimulator with a multiple-prong configuration according to principles described herein.

FIG. 2 illustrates a stimulator with a multiple-prong configuration according to principles described herein. As shown in FIG. 2, the stimulator (100) includes two prongs (102) that extend from a base (101). The base (101) may be used to house the principal electronic components of the stimulator, for example, the rechargeable battery (16, FIG. 1), the communication coil (18, FIG. 1) and the other electronic components (14, FIG. 1). The housing of the base (101) may be made, for example, from titanium. However, if the coil (18) is housed in the base (101), the base (101) may be partially or entirely made of ceramic or other material that will better support operation of the coil (18) as described herein.

One or more suture loops (105) may also be formed or disposed on the stimulator (100) to assist a physician in securing the stimulator (100) at a target site within the patient. When the stimulator (100) is implanted, the surgeon places sutures through the suture loop or loops (105) to secure the stimulator (100) to the site where stimulation is to be provided. Additionally or alternatively, a wide variety of means may be employed to secure the stimulator (100) at the target site. Tines, coating and other means of fixation may be used at any part of the stimulator (100) to secure the stimulator (100) at the target sites.

Two prongs (102) extend from the base (101). As shown in FIG. 2, the prongs (102) may be substantially parallel. A channel (104) is thus formed between the two prongs (102). These prongs (102) may be formed of ceramic material.

The prongs (102) are used to support the electrodes (103) of the stimulator (100). The electrodes (103) may be formed, for example, of titanium or other conducting electrode material. The electrodes (103) are also electrically connected to the electrical components of the stimulator, which may be housed in the base (101), for example. In some examples, the titanium of the electrodes (103) extends to the base (101) for electrical connection to the components of the stimulator.

A parylene coating (106) or other insulating material is selectively applied over the titanium except where the desired electrode surfaces (103-1, 103-2) are located, for example, at the ends of the prongs (102). The electrode surfaces (103-1, 103-2) are not covered by the parylene coating (106). A further explanation of the formation and placement of the electrodes will be provided below.

With the electrodes (103) being located on the prongs (102), the anode (103-1) and cathode (103-2) are relatively closer together than has been the case with previous stimulators. This allows the stimulator (100) to create a larger current gradient for stimulation than would be available if the electrodes (103) were further apart. For some treatment applications, the increased gradient may be advantageous or necessary.

Additionally, dual-channel bipolar stimulation can be achieved with the stimulator of FIG. 2. Where bipolar stimulation is desired, the base (101), or a portion thereof, functions as a reference, with simulation then being selectively output using the two electrodes (103) on the prongs (102).

Current steering can be achieved by selectively balancing or adjusting the current that is output, respectively, by the two or more separate electrodes (103-1, 103-2). Current steering is described in further detail in co-pending U.S. patent application Ser. No. 10/641,905, entitled "An Implantable Pulse Generator Having Current Steering Means," filed Aug. 15, 2003 and incorporated herein by reference in its entirety.

Figure 3:
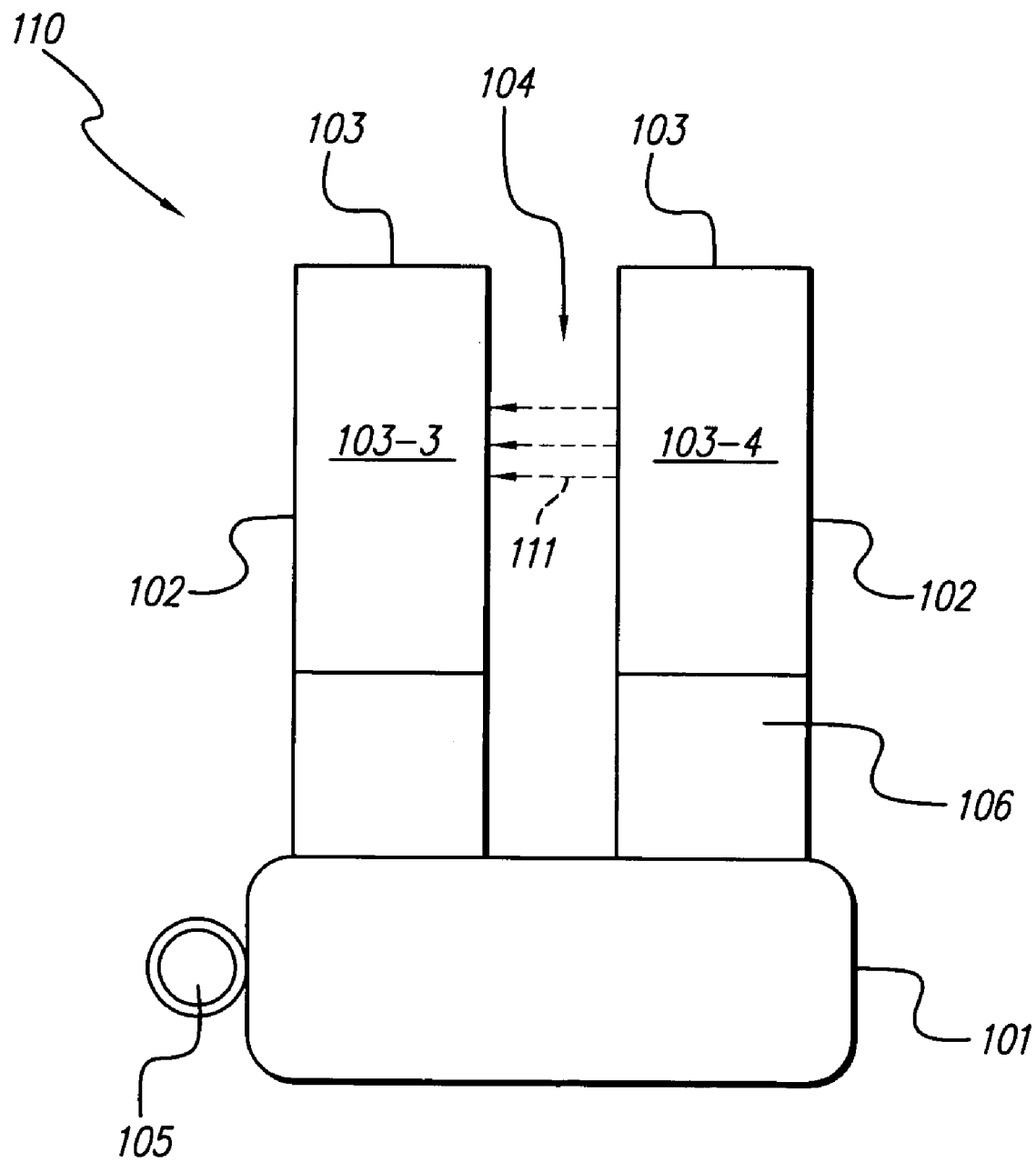
FIG. 3 illustrates another stimulator with a multiple-prong configuration according to principles described herein.

FIG. 3 illustrates another stimulator with a multiple-prong configuration according to principles described herein. As shown in FIG. 3, a base (101) houses the principal electronic components of the stimulator (110) and supports two prongs (102), as described above.

However, the electrodes (103-3, 103-4) are not located exclusively at the ends of the prongs (102). As shown in FIG. 3, the electrode surfaces (103-3, 103-4) may be formed to include the ends of the prongs (102) and to extend from the ends of the prongs down along some upper portion of the prongs (102). In other embodiments, the electrodes (103) may not include the ends of the prongs (102), but may just be formed at desired locations along the lengths of the prongs (102). As will be appreciated by those skilled in the art, the electrodes can be formed over any portions of the respective lengths of the prongs (102) of the stimulator (110). In any event, parylene coating (106) is formed over those portions of the prongs (102) which are not an electrode surface.

As noted above, the stimulator (110) may be positioned so that the tissue being stimulated, such as a nerve, extends through the channel (104) between the prongs (102) and between the electrodes (103-3, 103-4) disposed along the length of the prongs (102). Where a particularly high current gradient (111) is useful, for example, the stimulator (110) may be positioned with the tissue being stimulated in the channel (104).

The active surface or electrodes of the stimulator can be arbitrarily formed over any portion or length of the prongs (102). A parylene coating is used to cover or mask portions of the prong (102) that are not used as an electrode surface.

Figure 4:
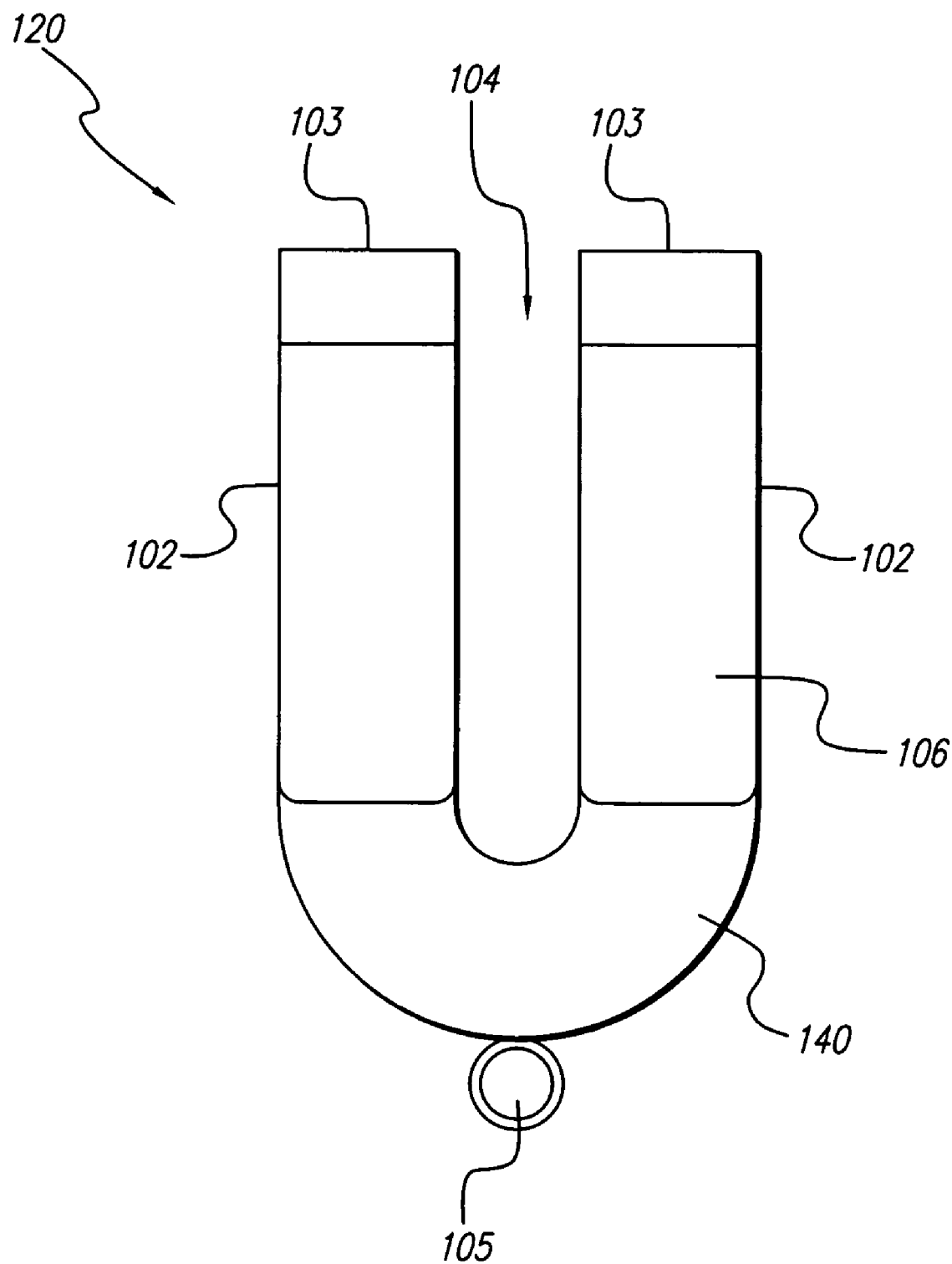
FIG. 4 illustrates another stimulator with a U-shaped configuration according to principles described herein.

FIG. 4 illustrates another stimulator with a U-shaped configuration according to principles described herein. As shown in FIG. 4, the base (101, FIG. 2) described above, can be replaced with a curved connector (140). This gives the stimulator (120) a U-shaped configuration which may be advantageous in some applications.

The curved connector (140) can contain the same components of the stimulator (120) as the base (101, FIG. 2) described above. The two prongs (102) extend from the connector (104) and support the electrodes (103) in the same manner described above. As before, the electrodes can be formed over any portion or length of the respective prongs (102) as desired for a particular application.

Figure 5:
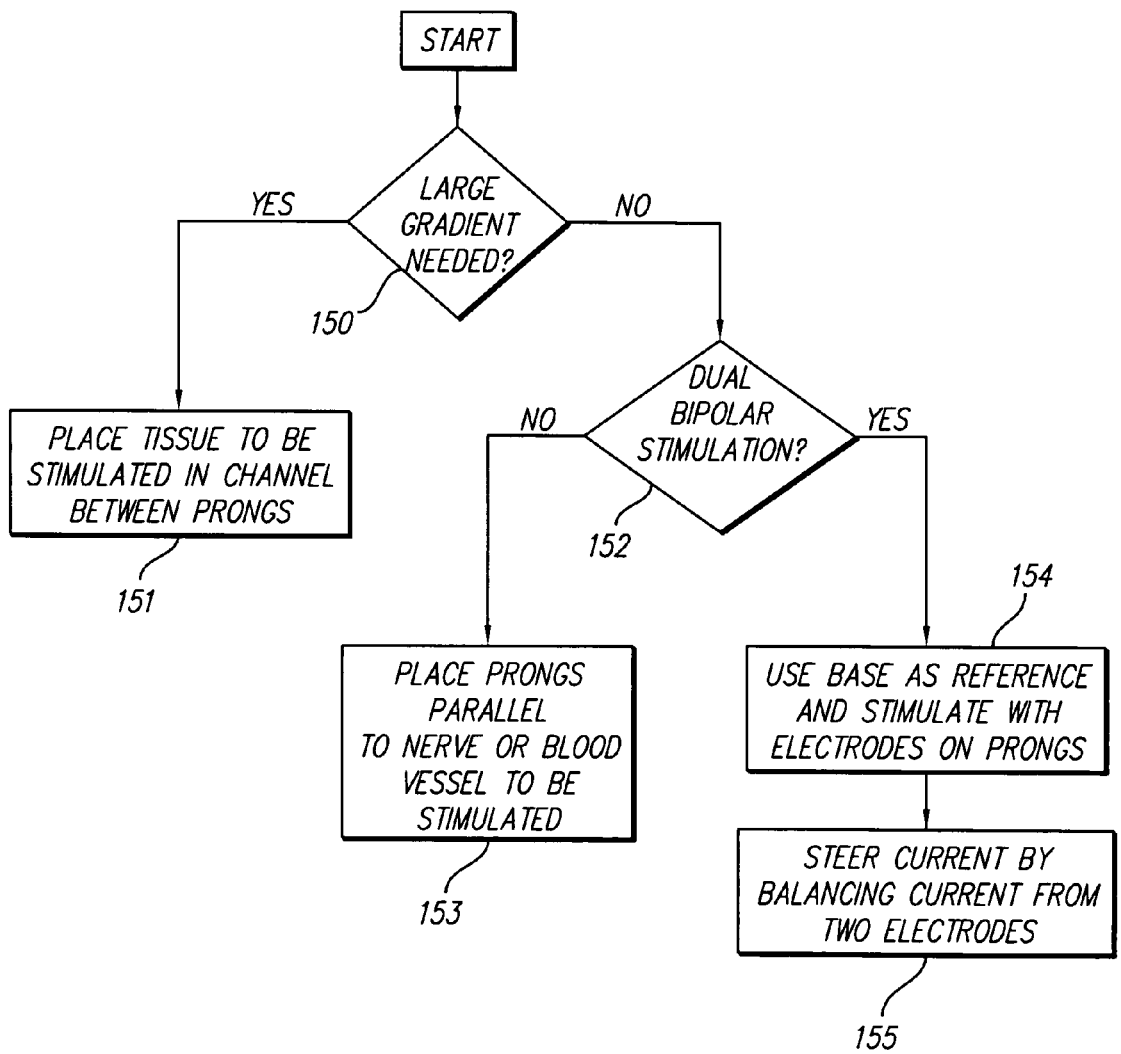
FIG. 5 is a flow chart illustrating some of potential uses of the stimulator configurations described herein.

FIG. 5 is a flow chart illustrating some of potential uses of the stimulator configurations described herein. As mentioned above, some patients will be best treated with a stimulation having a relatively large current gradient (determination 150). Depending on the current gradient needed, it may be advantageous to place the tissue being stimulated in the channel between the prongs of a stimulator like those described above (step 151).

In other instances, dual-channel bipolar stimulation may be needed (determination 152). Where this is the case, the base of the two-prong stimulator can be used as a reference with bipolar stimulation being provided selectively by the two electrodes on the prongs (step 154). Current steering can be achieved by selectively balancing or adjusting the current that is output, respectively, by the two separate electrodes (step 155).

In other instances, it may be advantageous to place the stimulator with the prongs running parallel to the tissue being stimulated (step 153). The tissue stimulated in such cases may be, for example, a nerve or blood vessel.

Figure 6:
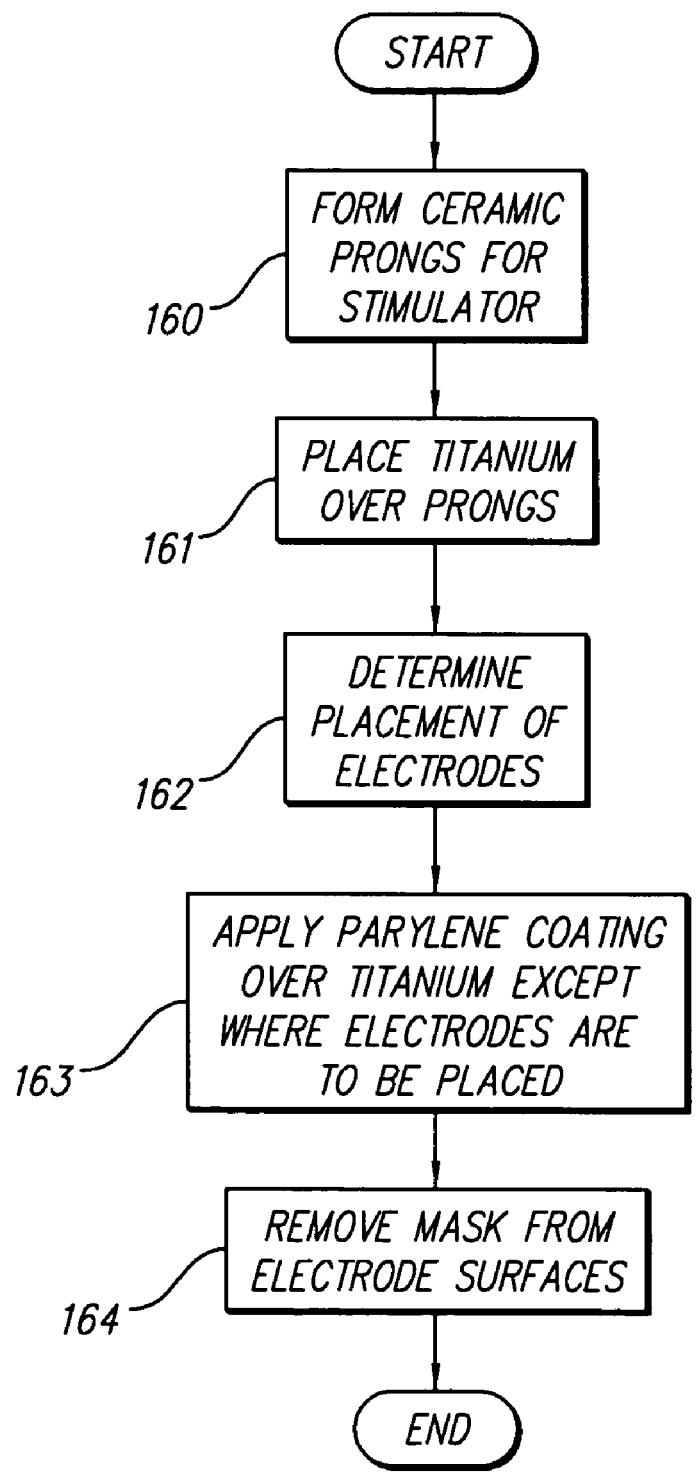
FIG. 6 is a flow chart illustrating an exemplary method of forming a stimulator according to principles described herein.

FIG. 6 is a flow chart illustrating an exemplary method of forming a stimulator according to principles described herein. As noted above, the active surface or electrodes of the stimulator can be arbitrarily formed over any portion or length of the prongs of a stimulator.

First, the prongs are formed (step 160). For example, the prongs may be formed of a ceramic material. Next, titanium or other electrode material is placed over the ceramic prongs (step 161). The titanium may cover the entirety of each prong and can be electrically connected to electronic components of the stimulator in the stimulator base. The prongs may be covered by titanium, for example, machining a titanium cover that slides over each of the prongs.

Next, a determination is made as to where the electrodes should be placed along the prongs and what size the electrodes should be (determination 162). As described above, the electrodes may be formed at the ends of the prongs only, may include the ends of the prongs and extend some distance down the length of the prongs, or may be formed only along some length of the prong and spaced some distance from the tips of the prongs. The shape, size and location of the electrodes on the prongs can be arbitrarily determined as best suits a particular application.

Next, a mask is formed on the prongs over the areas that will be the electrode surfaces. Then, a parylene coating is applied (step 163). The parylene coating may be applied by chemical vapor deposition. The mask, and the parylene coating on the mask, is then removed from the electrode surfaces (step 164). In this way, a parylene coating is applied that covers and insulates the titanium or other electrode material on the prongs in all areas except where the titanium is to be exposed and form an electrode surface.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A device comprising:
an implantable stimulator comprising:
  a base comprising a housing;
  two ceramic prongs extending laterally from a same side of said base; and
  an electrode disposed on each of said prongs,
  wherein said housing houses electrical components of the implantable stimulator, the electrical components being configured to generate an electrical potential for output by the electrodes,
  wherein at least one of the ceramic prongs comprises:
  a solid ceramic member;
  an electrical conductor covering at least a portion of the solid ceramic member, wherein the electrical conductor is electrically connected to a one of the electronic components of the stimulator in the base; and
  an electrically insulating material insulating at least a portion of the electrical conductor.

2. The device of claim 1, wherein said base is a curved connector giving said stimulator an overall U-shape.

3. The device of claim 2, wherein a thickness of the device is substantially uniform along the U-shape of the stimulator.

4. The device of claim 1, wherein said prongs extend parallel to each other and side-by-side.

5. The device of claim 1, wherein said electrodes are discrete elements disposed at ends of said prongs.

6. The device of claim 1, wherein said electrodes are discrete elements disposed along respective lengths of said prongs.

7. The device of claim 1, further comprising at least one suture loop fixedly attached to the implantable stimulator.

8. The device of claim 1, wherein said electrodes comprise titanium electrodes.

9. The device of claim 1, wherein said housing comprises a titanium housing.

10. The device of claim 1, wherein said stimulator comprises electrical circuitry configured to output dual-channel bipolar stimulation using said electrodes on said two prongs.

11. The device of claim 1, wherein the electrical conductor comprises a covering over the entirety of the solid member.

12. The device of claim 1, wherein the two prongs comprise generally parallel, solid elongate elements that extend outwardly from the base to define a channel therebetween, wherein the channel is dimensioned to receive a nerve to be stimulated.

13. The device of claim 1, wherein the base comprises a curved solid member having a first end and a second end, wherein the first end is connected to a first of said prongs and the second end is connected to a second of said prongs.

14. The device of claim 1, wherein the implantable stimulator is implantable as a unit beneath a patient's skin.

15. The device of claim 1, wherein said housing houses a battery and a coil.

16. The device of claim 1, wherein:
the base comprises an elongate housing; and
the prongs extend laterally from said base.

17. The device of claim 1, wherein:
the implantable stimulator is implantable as a unit beneath a patient's skin;
the housing comprises an elongate housing;
the electrical components are configured to generate a potential suitable for stimulating a nerve;
the two prongs are spaced apart to define a channel therebetween;
the electrodes are electrically coupled to the electrical components housed within the elongate housing for output the electrical potential from the implantable stimulator; and
the channel is dimensioned to receive a nerve to be stimulated by the electrical potential output from the electrodes.

18. A device comprising:
an implantable stimulator comprising:
  a base comprising a housing;
  two ceramic prongs extending laterally from a same side of said base; and
  an electrode disposed on each of said prongs,
  wherein said housing houses electrical components of the implantable stimulator, the electrical components being configured to generate an electrical potential for output by the electrodes,
  wherein at least one of the ceramic prongs comprises:
  a solid member;
  an electrical conductor covering at least a portion of the solid member, wherein the electrical conductor is electrically connected to a one of the electronic components of the stimulator in the base, wherein the electrical conductor comprises a conductive cover dimensioned to slidably receive the solid member; and
  an electrically insulating material insulating at least a portion of the electrical conductor.

* * * * *